(12) United States Patent
Colman et al.

(10) Patent No.: US 7,807,860 B2
(45) Date of Patent: Oct. 5, 2010

(54) AUTOTHERMAL CRACKING PROCESS AND REACTOR

(75) Inventors: Derek Alan Colman, Hampshire (GB); Michael John Alexander Matthewman, Surrey (GB); Ian Allan Beattie Reid, London (GB); Vaughan Clifford Williams, Middlesex (GB); William Terence Woodfin, Hampshire (GB)

(73) Assignee: Ineos Europe Limited, Hampshire (GB)

( * ) Notice: Subject to any disclaimer, the term of this patent is extended or adjusted under 35 U.S.C. 154(b) by 1106 days.

(21) Appl. No.: 10/543,696

(22) PCT Filed: Feb. 6, 2004

(86) PCT No.: PCT/GB2004/000488

§ 371 (c)(1),
(2), (4) Date: Jul. 28, 2005

(87) PCT Pub. No.: WO2004/074222

PCT Pub. Date: Sep. 2, 2004

(65) Prior Publication Data

US 2006/0149114 A1    Jul. 6, 2006

(30) Foreign Application Priority Data

Feb. 18, 2003    (GB) .................................. 0303723.1
Dec. 22, 2003    (GB) .................................. 0329710.8

(51) Int. Cl.
*C07C 5/333* (2006.01)

(52) U.S. Cl. ........................ 585/658; 585/652; 585/654; 585/660; 422/191; 422/198; 422/220; 260/683.3

(58) Field of Classification Search ................. 585/652, 585/654, 658, 660; 422/191, 198, 220; 260/683.3
See application file for complete search history.

(56) References Cited

U.S. PATENT DOCUMENTS 3,320,331 A  *  5/1967  Gaspar et al. ............... 502/209

(Continued)

FOREIGN PATENT DOCUMENTS

EP            0 332 289 A       9/1989

(Continued)

*Primary Examiner* — Glenn Caldarola
*Assistant Examiner* — Prem C. Singh
(74) *Attorney, Agent, or Firm* — Nixon & Vanderhye (57) ABSTRACT

The present invention provides a reactor design that enables an auto-thermal cracking process to be conducted at any suitable pressure wherein the gaseous reactants are preheated separately before mixing and then presented to the reaction zone in a uniformly distributed manner. In particular, the present invention-relates to apparatus for reacting a first and second gaseous reactant to form a gaseous product wherein the apparatus comprises at least one first supply means for the first gaseous reactant, at least one second supply means for the second gaseous reactant, a resistance zone and a reaction zone, preferably comprising a catalyst, wherein the first supply means comprises a plurality of first outlets for delivery of the first gaseous reactant, and the second supply means comprises a plurality of second outlets for delivery of the second gaseous reactant, the resistance zone is porous, the reaction zone is positioned downstream of the resistance zone with respect to the flow of the first and second gaseous reactants and wherein the first supply means and the second supply means are arranged such that the first gas and the second gas are contacted in an essentially parallel manner and mixed prior to contacting the resistance zone. The present invention also provides a process for the production of a mono-olefin utilizing said apparatus.

30 Claims, 2 Drawing Sheets

U.S. PATENT DOCUMENTS

| | | |
|---|---|---|
| 3,881,701 A | 5/1975 | Schoenman et al |
| 4,865,820 A | 9/1989 | Dunster et al. |
| 5,106,590 A | 4/1992 | Hopper et al. |
| 2002/0098136 A1 | 7/2002 | Vanderborgh |

FOREIGN PATENT DOCUMENTS

| | | |
|---|---|---|
| EP | 0 706 446 A | 10/2000 |
| EP | 1 382 382 A1 | 1/2004 |
| SU | 255912 A | 7/1968 |
| SU | 435633 | 6/1982 |
| WO | WO 96/19424 | 6/1996 |
| WO | WO 97/26987 | 7/1997 |
| WO | WO 98/49095 | 11/1998 |
| WO | WO 00/37171 | 6/2000 |
| WO | WO 01/12312 | 2/2001 |
| WO | WO 01/47842 | 7/2001 |
| WO | WO 01/47843 | 7/2001 |
| WO | WO 01/83405 | 11/2001 |
| WO | WO 01/83405 A | 11/2001 |

* cited by examiner

AUTOTHERMAL CRACKING PROCESS AND REACTOR

This application is the U.S. National Phase of International Application PCT/GB04/000488,filed 6 Feb. 2004,which designated the U.S. PCT/GB04000488 claims priority to British Application No. 0303723.1, filed 18 Feb. 2003, and British Application No. 0329710.8, filed 22 Dec. 2003. The entire content of these applications are incorporated herein by reference.

The present invention relates to a reactor suitable for the production of olefins by auto-thermal cracking.

BACKGROUND OF THE INVENTION

Auto-thermal cracking is a known process for the production of olefins. An example of such a process is described in EP-A-0 332 289. In this process, a hydrocarbon and an oxygen-containing gas are contacted with a catalyst, which is capable of supporting combustion beyond the fuel rich limit of flammability. The hydrocarbon is partially combusted, and the heat produced is used to drive the dehydrogenation of the hydrocarbon feed into olefins.

In the auto-thermal cracking process the hydrocarbon and the oxygen-containing gas may be uniformly mixed and preheated prior to contacting the catalyst. However mixing and preheating the hydrocarbon and oxygen-containing gas becomes problematic if it is desired to carry out the process at elevated pressure due to flammability constraints. Thus, it becomes desirable to reduce the time between forming the mixture of hot gaseous reactants and contacting the mixture with the catalyst.

SUMMARY OF THE INVENTION

The present invention provides a reactor design that enables an auto-thermal cracking process to be conducted at any suitable pressure wherein the gaseous reactants are preheated separately before mixing and then presented to the reaction zone in a uniformly distributed manner.

Accordingly the present invention provides apparatus for reacting a first gaseous reactant with a second gaseous reactant to form a gaseous product, wherein the apparatus comprises at least one first supply means for the first gaseous reactant, at least one second supply means for the second gaseous reactant, a resistance zone and a reaction zone, preferably comprising a catalyst, and wherein the first supply means comprises a plurality of first outlets for delivery of the first gaseous reactant, and the second supply means comprises a plurality of second outlets for delivery of the second gaseous reactant, the resistance zone is porous, is positioned downstream of the first and second supply means with respect to the flow of the first and second gaseous reactants and is in fluid communication with the first and second supply means, the reaction zone is positioned downstream of the resistance zone with respect to the flow of the first and second gaseous reactants and is in fluid communication with the resistance zone, and wherein the first supply means and the second supply means are arranged such that the first gas and the second gas are contacted in an essentially parallel manner and mixed prior to contacting the resistance zone.

Preferably, the first supply means comprises at least one first inlet for supplying a first gaseous reactant to at least one first manifold and a plurality of first outlets exiting the first manifold for delivery of the first gaseous reactant, and the second supply means comprises at least one second inlet for supplying a second gaseous reactant to at least one second manifold and a plurality of second outlets exiting the second manifold for delivery of the second gaseous reactant.

The apparatus suitably comprises at least 100, preferably at least 500, most preferably at least 1000, first and second outlets per meter squared of the transverse cross section of the reaction zone.

The first and second supply means are arranged such that the first and second gas are contacted in an essentially parallel manner. By "essentially parallel manner" is meant that the first and second gas, when they are brought into contact, are both flowing in essentially the same direction, such as axially, rather than flowing in opposite or tangential relative directions. Contacting the gases in an essentially parallel manner, rather than, for example, in a tangential manner, provides reduced turbulence in the region where the gases first contact (where mixing is not yet complete, and the compositions of gases present can vary significantly).

Turbulence can increase the residence time of mixed gas in the reactor, which increases the risk of flammability problems arising. In some cases, contacting the gases in a perpendicular manner can lead to regions of low flow, or even stagnant regions, containing flammable gas mixtures close to the contacting region. Contacting the gases in an essentially parallel manner according to the present invention reduces the potential for regions of low flow mixed gas, reducing the potential for flammability problems.

In a first embodiment of the invention the contacting/mixing arrangement is provided by positioning one supply means within the other and providing at least a portion of the supply means located within the other with suitable openings such that one gaseous reactant can pass through the openings and contact the other gaseous reactant.

Preferably, the first embodiment of the invention provides apparatus wherein the first supply means comprises at least one first inlet for supplying a first gaseous reactant to at least one first manifold and a plurality of injection tubes exiting said first manifold for delivery of the first gaseous reactant, and the second supply means comprises at least one second inlet for supplying a second gaseous reactant to at least one second manifold and a plurality of conduits exiting said second manifold for delivery of the second gaseous reactant, wherein the second manifold is positioned downstream of the first manifold with respect to the flow of the first gaseous reactant, the resistance zone is porous, is positioned downstream of the second manifold with respect to the flow of the first and second gaseous reactants and is in fluid communication with the conduits exiting the second manifold, the reaction zone is positioned downstream of the resistance zone with respect to the flow of the first and second gaseous reactants and is in fluid communication with the resistance zone, and wherein each conduit comprises an upstream end exiting the second manifold and a downstream end in fluid communication with the resistance zone and wherein the injection tubes exiting the first manifold are arranged such that they extend through the second manifold and project axially into the upstream end of the conduits.

Advantageously the apparatus of the first embodiment usually comprises a first cooling zone contacting the downstream end of the plurality of conduits exiting the second manifold arranged such that the downstream end of the plurality of conduits are cooled. This ensures that the gaseous reactants are prevented from reacting until they enter the reaction zone.

Furthermore the apparatus of the first embodiment usually comprises a product cooling zone downstream of the reaction zone such that the gaseous products can be cooled upon exiting the reaction zone.

In the first embodiment of the invention, preferably, the first manifold is a first chamber and the second manifold is a second chamber and the injection tubes exiting the first chamber form a plurality of elongated passageways extending through the second chamber into the upstream end of the plurality of conduits exiting the second manifold.

The volumes of the first and second chambers are not especially critical. However, in a preferred embodiment, the volumes of the first and second chambers are adapted to be relatively small for safety reasons. Typically when the reactor diameter is 600 mm the volume of the first chamber is usually between 5-100 liters, preferably: between 10-40 liters and more preferably between 15-25 liters e.g. 22 liters. The volume of these chambers will be proportional to the cross-sectional area of the reactor (i.e. diameter squared)

Typically when the reactor diameter is 600 mm the volume of the second chamber is usually between 20-200 liters, preferably between 30-100 liters and more preferably between 40-80 liters e.g. 50 liters.

The apparatus of the first embodiment usually comprises an equal number of injection tubes and conduits, each injection tube projecting into a corresponding conduit. Preferably the apparatus comprises at least 100, preferably at least 500, most preferably at least 1000 injection tubes per meter squared of the transverse cross section of the reaction zone.

So as to allow the injection tubes to project into the conduits the external diameter of the injection tubes where they project into the conduits is less than the internal diameter of the conduits. The exact external diameter is not critical to the invention, but usually the injection tubes have an external diameter of between 2.0 to 5.0 mm, e.g. 4.0 mm. The injection tubes have a length sufficient to extend through the second chamber (i.e. typically greater than 170 mm).

At the end of each of the plurality of injection tubes remote from the manifold, the first gaseous reactant can exit the tubes through a suitable opening, preferably a nozzle, and which has a diameter less than the external diameter of the injection tube, preferably between 0.5 to 3.0 mm, such as between 1.0 to 2.0 mm. The nozzle, when present, preferably has a diameter less than the internal diameter of the injection tube other than at the nozzle, hence providing a restriction that assists in obtaining even flow rates from all injection tubes, without providing the pressure drop characteristics that would be obtained if the internal diameter of the injection tube was this size for a significant length of the injection tube.

Usually the conduits have an internal diameter of between 1 to 10 mm, preferably between 2 to 8 mm e.g. 7 mm and a length of between 50 to 500 mm, preferably between 100 to 300 mm e.g. 210 mm. The conduits may be arranged in a symmetrical configuration such as in a triangular or square configuration.

The ratio of the inner diameter of the conduits to the diameter of the opening, e.g. nozzle, of the injection tubes is suitably in the range 2:1 to 10:1, for example, in the range 3:1 to 5:1.

Where the injection tubes of the first supply means extend through the manifold of the second supply means, each injection tube may be provided with an outer tube, around the injection tube (which forms an inner tube within said outer tube). The outer tube provides thermal insulation from the second gaseous reactant when this is at a different temperature than the first gaseous reactant (which passes along the inside of the inner tube).

In a further preferred embodiment, suitable flow restrictors are also provided between the outer surface of the injection tubes and the inner surface of the conduits, at a location at or close to where the injection tubes enter the conduits at the upstream end of the conduits (i.e. close to the second manifold). These flow restrictors may be located on the injection tubes and/or on the conduits, and, by providing resistance, they assist in obtaining even flow rates of the second gaseous reactant into each conduit. These flow restrictors should be located remote from the exits of the first injection tubes such that the velocity of the second gaseous reactant, which has a maximum velocity in the conduit when passing through or past the flow restrictors, has reduced (from that maximum) when mixed with the first gaseous reactant. Preferably the pressure drop of the flow passing these restrictions is of similar order as the pressure drop of the first gaseous reactant through the nozzles or other restrictions at the end of the injection tubes (such as 1 bar and 0.5 bar respectively). This ensures that the proportions of the reactants entering the reaction zone remain similar when there are small fluctuations in pressures in the reaction zone or in the feeds. For optimum yields, the tolerance on the nozzle diameters and the flow restrictors for the second gaseous reactant should be such that the concentration of the gaseous mixture varies by no more than 5%.

Typically, between 5-40 mm, preferably between 10-30 mm, and most preferably between 15-25 mm e.g. 20 mm of the length of the injection tube projects axially into the conduit.

Wherein the apparatus of the first embodiment comprises a first cooling zone the first cooling zone is preferably provided by contacting a cooling fluid with the external surface area of the downstream end of the conduits. Typically, 10-20% of the external surface area of the conduit may be contacted with the cooling fluid.

In a second embodiment of the present invention, the contacting/mixing arrangement is provided by a first supply means comprising at least one first inlet for supplying a first gaseous reactant to at least one first manifold and a plurality of first injection tubes exiting said first manifold for delivery of the first gaseous reactant, and a second supply means comprising at least one second inlet for supplying a second gaseous reactant to at least one second manifold and a plurality of second injection tubes exiting said second manifold for delivery of the second gaseous reactant, wherein each injection tube has an exit at the end remote from the manifold and which has a cross-sectional opening of 1 $mm^2$ or less, and wherein the exits from the first and second injection tubes are in an intermixed configuration.

By intermixed, as used herein, is meant that the exits of the plurality of first injection tubes are dispersed amongst the exits of the plurality of second injection tubes and/or vice versa. Thus, for example, where there are more first injection tubes than second injection tubes, the exits of the second injection tubes will be dispersed amongst the exits of the first injection tubes and the optimal configuration for the exits for the second injection tubes will be such that each second injection tube will have the exit of at least one first injection tube as its nearest neighbour.

Suitably, there are at least 10000 first and second injection tubes in total per square meter. The use of said number of intermixed tubes provides rapid mixing at the outlets of said tubes.

For optimal delivery of the first and second gaseous reactants to the resistance zone, the exits from the injection tubes of the second embodiment should all be located in an essentially planar configuration.

The exits of the first injection tubes may be arranged in a symmetrical configuration, such as in a triangular, square, rectangular or hexagonal configuration and/or the exits of the second injection tubes may be arranged in a symmetrical configuration, such as in a triangular, square, rectangular or hexagonal configuration.

In this second embodiment, the exits may be any suitable shape in cross-section, such as triangular, rectangular, square, hexagonal, D-shaped, oval or circular.

Mixing of the gases becomes more rapid as the number of tubes is increased and the cross-sectional opening of the exits of the tubes is decreased.

Thus in a preferred aspect of the second embodiment of the present invention, each injection tube has an exit at the end remote from the manifold which has a cross-sectional opening of 0.5 mm$^2$ or less. More preferably the exits have a cross-sectional opening of 0.2 mm$^2$ or less, such as 0.1 mm$^2$ or less. Suitably, the exits have a cross-sectional opening of 0.004 mm$^2$ or more.

The exits for the injection tubes for one reactant may vary in size and shape but are preferably the same. Similarly, the exits for the second gaseous reactant may be different to, or may be the same size and shape as the exits for the first gaseous reactant.

Most preferably, the exits are D-shaped, such as semi-circular, with a cross-sectional opening of between 0.01 mm$^2$ and 0.05 mm$^2$.

The apparatus of this second embodiment may comprise an equal number of first and second injection tubes for delivery of said first and second gaseous reactants respectively. Alternatively, the relative number of injection tubes for delivery of each gaseous reactant may be different, for example, the relative number of injection tubes for delivery of each gaseous reactant may be in proportion to the relative amount of each gaseous reactant to be delivered. However, the relationship between the numbers of tubes is not critical to the invention, and, for example, the velocities of the first and second gaseous reactants exiting the respective injection tubes may be, and preferably are, different. In particular, the use of differing flow rates for each of the first and second gaseous reactants allows different ratios of said first and second gaseous reactants to be achieved utilizing a fixed number of injection tubes for each reactant.

Preferably, one of the reactants, more preferably the reactant with lowest molecular mass, exits one set of the injection tubes with a higher velocity than the other reactant exits the other injection tubes. For example, the size and number of the injection tubes for one reactant may be such that the ratio of the exit velocities is at least 10:1 for example the exit velocity of one reactant is at least 100 m/s while the number and size of the injection tubes for the other reactant may be such that the exit velocity is less than 10 m/s. The mean velocity of the combined flows having exited the injection tubes may be of the order of 3 m/s.

As the cross-sectional opening of the exit tubes decreases, so the number of first and second injection tubes per unit area of the transverse cross-section of the reaction zone can increase. Thus, the apparatus of the second embodiment may comprise at least 100000, for example at least 1000000, such as 4000000 injection tubes (total of first and second injection tubes) per square meter of the transverse cross section of the reaction zone.

Similarly, the distance between one exit and its nearest neighbour will also decrease as the cross-sectional opening of the exit tubes decreases and the number of first and second injection tubes increases. Thus, the distance between one exit and its nearest neighbour in this second embodiment may be less than 2000 microns, such as less than 1000 microns and preferably in the range 100 to 500 microns. The distance between neighbouring tubes is preferably of similar dimension to the exits themselves, such as in the range from one half to twice the maximum dimension across the opening of the exit.

By using the intermixed arrangement of the first and second injection tubes with relatively small exit holes according to the second embodiment of the present invention, for delivery of the first and second gaseous reactants respectively, rapid mixing of the first and second gaseous reactants is achieved. Typically, by using an intermixed arrangement of the first and second injection tubes with exits with a cross-sectional opening of 0.5 mm$^2$ or less, adequate mixing may be achieved in a distance of less than 5 mm from the exits of the injection tubes, allowing the gases to be mixed and contacted with the resistance zone in a short space, and, hence, within a short period of time.

The apparatus of the second embodiment usually comprises a product cooling zone downstream of the reaction zone, such that the gaseous products can be cooled upon exiting the reaction zone.

Preferably, in the second embodiment of the invention, the first manifold comprises a first chamber and the second manifold comprises a second chamber, with the respective first and second gaseous components exiting therefrom and into a plurality of first and second injection tubes. The injection tubes with exits with a cross-sectional opening of 1 mm$^2$ or less are preferably formed as passageways in a diffusion bonded block. Diffusion bonded blocks formed by diffusion bonding of layers of etched metal structures are known for heat exchange uses, and are described generally, for example, in "Industrial Microchannel Devices—Where are We Today?"; Pua, L. M. and Rumbold, S. O.; First International Conferences on Microchannels and Minichannels, Rochester, N.Y., April 2003.

The use of diffusion bonding techniques in the present invention allows a plurality of passageways to be formed connecting the first and second chambers respectively to a plurality of first and second exits, the exits being in an intermixed configuration, as required for forming the injection tubes of the second embodiment of the present invention.

As with the first embodiment, the volume of the first and second chambers are not especially critical, but, preferably, the volume of the first and second chambers in the second embodiment are adapted to be relatively small for safety reasons.

After mixing according to the process of the present invention, either by the apparatus of the first or second embodiment, or otherwise, the mixed first and second gaseous reactants are contacted with a resistance zone positioned downstream of first and second supply means.

The resistance zone is porous. The permeability of the porous resistance zone ensures dispersion of the fluid reactants as they pass through the zone. The fluids move through a network of channels laterally as well as axially (axially being the general direction of flow of the reactants through the resistance zone), and leave the resistance zone substantially uniformly distributed over the cross-sectional area of the resistance zone.

Preferably, the resistance zone is as permeable laterally as it is axially. More preferably the resistance zone has a permeability which is substantially the same in any direction, such as having a permeability in any direction which is from 0.2 to 5 times the permeability in any other direction.

Methods are known for determining the permeability of porous media. The pressure gradient or pressure drop per unit length through the resistance zone may be defined using the inertial resistance coefficient where the pressure gradient equals the product of the inertial resistance coefficient and the dynamic pressure. The dynamic pressure is half the product of the fluid density and the square of the superficial velocity and has units of pressure. The inertial resistance coefficient has units of reciprocal length. The resistance zone usually has an average inertial resistance coefficient (i.e. averaged over all directions) of between 500-10000/meter (/m), preferably between 2000-4000/m and advantageously between 2500-3500/m e.g. 3250/m.

The resistance zone may be formed of a porous metal structure, but preferably the porous material is a non metal e.g. a ceramic material. Suitable ceramic materials include lithium aluminium silicate (LAS), alumina ($\alpha$-$Al_2O_3$), yttria stabilised zirconia, alumina titanate, niascon, and calcium zirconyl phosphate. A preferred porous material is gamma alumina.

The distance of the resistance zone from the ends of the conduits in the first embodiment and the exit of the tubes in the second embodiment is preferably less than 20 mm, more preferably between 1 and 10 mm, more preferably between 1.5 and 5 mm, such as 2 mm.

Wherein the reaction zone comprises a supported catalyst preferably the porous material in the resistance zone may be the same as the porous material used as the catalyst support. The porous material may be in the form of spheres, other granular shapes or ceramic foams. The reaction zone may comprise a supported catalyst in the form of a monolith providing a continuous multichannel structure.

For the porous material in the resistance zone, advantageously at least 70%, preferably at least 80% and advantageously at least 90% of the pores have a pore width of less than 5.0 mm e.g. usually between 0.1-3.0 mm, preferably between 0.2-2.0 mm and most preferably between 0.5-1.5 mm.

Typically the resistance zone has between 10-60 pores per square inch, preferably between 20-50 pores per square inch and most preferably between 30-45 pores per square inch.

Usually the depth of the resistance zone is between 5-100 mm but is preferably 10-50 mm.

Usually the reaction zone has a depth of between 10-200 mm but is preferably 20-100 mm e.g. 60 mm. Preferably the reaction zone comprises a catalyst.

(The depth of the resistance zone and the reaction zone are measured in the direction of flow of the reactant gases. In general, the preferred depths are defined by the flow rate of the reactant gases, since this determines the contact time, and, as with other dimensions measured in the direction of gas flow, are, for most practical purposes, independent of reactor cross-section.)

When a catalyst is employed suitably the catalyst is a supported platinum group metal. Preferably, the metal is either platinum or palladium, or a mixture thereof. Although a wide range of support materials are available, it is preferred to use alumina as the support. The support material may be in the form of spheres, other granular shapes or ceramic foams. Preferably, the support is a monolith which is a continuous multichannel ceramic structure, frequently of a honeycomb appearance. A preferred support for the catalytically active metals is a gamma alumina. The support is loaded with a mixture of platinum and palladium by conventional methods well known to those skilled in the art. The resulting compound is then heat treated to 1200° C. before use. catalyst promoters may also be loaded onto the support. Suitable promoters include copper and tin.

The catalyst is usually held in place in the reactor in a suitable holder, such as a catalyst basket. Preferably, to prevent gas by-passing the catalyst between the catalyst and the holder, any space between the catalyst and the holder is filled with a suitable sealing material. Suitable sealing materials include man made mineral wools e.g. ceramic wool, which can be wrapped around the edges of the catalyst in the holder. In addition the catalyst may be coated around the edge with a material similar to the main catalyst support material, such as alumina, to aid this sealing.

The apparatus may comprise a product cooling zone downstream of the reaction zone, such that the gaseous products can be cooled upon exiting the reaction zone. The product cooling zone may be provided by one or more injection nozzles that are capable of injecting a condensate into the product stream exiting the reaction zone.

Preferably the first and second manifolds, the injection tubes, the conduits (if present), the housing for the resistance zone and the reaction zone are metallic e.g. steel. Where pure oxygen is employed as a gaseous reactant it may be necessary to make or coat some or all of any part of the apparatus that may contact the oxygen from/with an alloy that resists reaction with oxygen. Reaction with oxygen is more likely when the temperature of the oxygen is high and/or the oxygen is at high velocity. Suitable alloys include monel.

Immediately downstream of the reaction zone, where the temperature of the products from the reaction is high, the preferred material of construction is a high nickel alloy, such as Inconel, Incaloy, Hastelloy or Paralloy. The metal may be formed into shape by one or more of the following techniques: static casting, rotational casting, forging, machining and welding.

The apparatus may comprise a suitable thermal sleeve to reduce thermal stresses on the apparatus immediately downstream of the reaction zone. Thermal stresses can occur where relatively rapid changes in temperature, either a rapid increase or decrease, occur inside an apparatus, for example, at start-up or shut-down. The inner surface of the wall of the apparatus heats or cools rapidly, but the outer surface heats or cools more slowly providing stress across the wall (the wall being relatively thick, for example, to cope with the pressure differential between the inside of and the outside of the apparatus). The use of a sleeve of thin material, which may be of a similar material to the wall of the apparatus, as a thermal sleeve inside the apparatus reduces the rate of temperature change that impacts the inner surface of the wall, and hence reduces the thermal stress.

The apparatus is advantageously employed to partially oxidize a gaseous feedstock. Preferably the first gaseous reactant is an oxygen containing gas and the second gaseous reactant is a gaseous paraffinic hydrocarbon.

The present invention also provides a process for the production of a mono-olefin utilizing the apparatus previously described.

Thus, utilizing the apparatus of the first embodiment, the invention provides a process for the production of a mono-olefin said process comprising passing an oxygen containing gas into a first manifold and injecting the oxygen-containing gas via a plurality of injection tubes into a plurality of conduits, passing gaseous paraffinic hydrocarbon via a second manifold into the plurality of conduits wherein the gaseous paraffinic hydrocarbon is contacted in an essentially parallel manner and mixed with the oxygen-containing gas, passing the gaseous mixture to a reaction zone via a porous resistance zone, and partially combusting in the reaction zone the gaseous mixture, preferably in the presence of a catalyst which is capable of supporting combustion beyond the fuel rich limit of flammability, to produce the mono-olefin.

Utilizing the apparatus of the second embodiment, the invention provides a process for the production of a mono-olefin said process comprising passing an oxygen containing gas from at least one first inlet via at least one first manifold to a plurality of first injection tubes and passing a gaseous paraffinic hydrocarbon from at least one second inlet via at least one second manifold to a plurality of second injection tubes, wherein each injection tube has an exit at the end remote from the manifold and which has a cross-sectional opening of 1 mm$^2$ or less, and wherein the exits from the first and second injection tubes are co-located in an intermixed configuration, passing the gaseous mixture to a reaction zone via a porous resistance zone, and partially combusting in the reaction zone the gaseous mixture, preferably in the presence of a catalyst which is capable of supporting combustion beyond the fuel rich limit of flammability, to produce the mono-olefin.

Preferred processes for the production of a mono-olefin utilize apparatus with the preferred features as previously described. Thus, for example, the preferred apparatus for a process utilizing the apparatus of the second embodiment is such that each injection tube has an exit at the end remote from the manifold which has a cross-sectional opening of 0.5 mm$^2$ or less. More preferably the exits have a cross-sectional opening of 0.2 mm$^2$ or less, such as 0.1 mm$^2$ or less.

In the process for the production of a mono-olefin from a feedstock comprising a gaseous paraffinic hydrocarbon, the paraffinic hydrocarbon may suitably be ethane, propane or butane. The paraffinic hydrocarbon maybe substantially pure or may be in admixture with other hydrocarbons and optionally other materials, for example methane, nitrogen, carbon monoxide, carbon dioxide, steam or hydrogen. A paraffinic hydrocarbon-containing fraction such as naphtha, gas oil, vacuum gas oil, or mixtures thereof, may be employed. A suitable feedstock is a mixture of gaseous paraffinic hydrocarbons, principally comprising ethane, resulting from the separation of methane from natural gas. A preferred feedstock is a paraffinic hydrocarbon principally comprising ethane which provides a product principally comprising ethylene as the mono-olefin.

As the oxygen-containing gas there may suitably be used either oxygen or air. It is preferred to use oxygen, optionally diluted with an inert gas, for example nitrogen. The ratio of the gaseous paraffinic hydrocarbon to the oxygen-containing gas mixture is usually from 5 to 20 times the stoichiometric ratio of hydrocarbon to oxygen-containing gas for complete combustion to carbon dioxide and water. The preferred composition is from 5 to 10 times the stoichiometric ratio of hydrocarbon to oxygen-containing gas.

Although the apparatus can be used at any pressure e.g. between 0-100 barg it is particularly useful at elevated pressure. The pressure at the first and second inlets is preferably between 10-50 barg, most preferably between 20-40 barg, and advantageously between 25-35 barg e.g. 30 barg.

The oxygen containing gas may be fed at ambient temperature, but is usually preheated to 50 to 150° C., preferably 80-120° C. e.g. 100° C. The oxygen containing gas is injected into the conduits or from the exits of the plurality of injection tubes at a velocity to prevent the possibility of a flame stabilizing on the exits of the injection tubes. Especially in the first embodiment of the present invention, the injection tubes may end in a suitable nozzle to increase the exit velocity The exit velocity is typically greater than 30 m/s, preferably greater than 50 m/s, and advantageously greater than 70 m/s.

The gaseous paraffinic hydrocarbon is usually preheated to 100 to 400° C., preferably 150-350° C. e.g. 300° C. and passed into the conduits or from the plurality of second injection tubes wherein it is intimately mixed with the oxygen containing gas. The gaseous paraffinic hydrocarbon enters the conduits or exits the plurality of second injection tubes at a velocity typically greater than 5 m/s, preferably greater than 15 m/s, and advantageously greater than 20 m/s.

In the first embodiment, the velocity of the oxygen containing gas exiting the injection tubes and the velocity of the gaseous paraffinic hydrocarbon passing into the conduits preferably has the ratio of at least 1.5:1, preferably at least 3:1 and most preferably less than 6:1, such as 4:1. This ratio ensures rapid mixing.

In the second embodiment, the ratio of the velocity of the oxygen containing gas exiting the first injection tubes and the velocity of the gaseous paraffinic hydrocarbon exiting the second injection tubes will depend on the relative ratios of numbers of first and second injection tubes, their relative sizes and the desired oxygen to paraffinic hydrocarbon ratio, but preferably the ratio is at least 0.1:1, preferably at least 1:1 and most preferably at least 5:1. Typically, the exit velocity of the oxygen containing gas is at least 50 m/s, especially at least 100 m/s. For example, the size and number of the injection tubes for the oxygen containing gas may be such that the exit velocity is at least 100 m/s while the number and size of the injection tubes for the gaseous paraffinic hydrocarbon may be such that the exit velocity is less than 10 m/s, and the mean velocity of the combined flows having exited the injection tubes maybe of the order of 3 m/s.

The temperature of the gaseous mixture is usually between 100 to 400° C., preferably 100 to 300° C. e.g. 200° C. In addition to passing the gaseous paraffinic hydrocarbon to the conduits or second injection tubes, other gases may also be passed to the conduits or second injection tubes e.g. hydrogen, carbon monoxide and/or carbon dioxide.

In the first embodiment, the gas mixture may be cooled by the first cooling zone wherein a coolant, such as water, is passed around the external surface area of the downstream end of the conduits; The cooling of the downstream end of the conduits prevents local heating of the conduit which eliminates the tendency for any "flame creep back" in the event of a stable flame being formed at the exit of the conduits.

The temperature of the coolant is typically between 20-200° C., and preferably between 80-120° C. e.g. 100° C. The coolant flow rate is manipulated such that the coolant temperature increase is less than 100° C., preferably less than 50° C., and most preferably less than 30° C.

The first cooling zone reduces the temperature of the gaseous mixture by at least 10° C., preferably by at least 20° C., and most preferably by at least 30° C.

In both embodiments the gaseous mixture is usually passed to the resistance zone at a mean cross-section velocity between 1.0-10.0 m/s, preferably between 2.0-6.0 m/s and most preferably between 2.5-3.5 m/s.

The gaseous mixture is usually passed to the reaction zone at a velocity between 1.0-10.0 m/s, preferably between 2.0-6.0 m/s and most preferably between 2.5-3.5 m/s.

The pressure drop through the resistance zone is typically between 0:01-0.2 bar, and preferably between 0.05-0.1 bar e.g. 0.08 bar.

The temperature in the reaction zone is usually greater than 500° C., for example greater than 650° C., typically greater than 750° C., and preferably greater than 800° C. The upper temperature limit may suitably be up to 1200° C., for example up to 1100° C., preferably up to 1000° C.

The products exit the reaction zone at a temperature greater than 800° C. e.g. greater than 900° C. and at a pressure usually between 10-50 barg, most preferably between 20-40 barg, and advantageously between 25-35 barg e.g. 30 barg.

Preferably the products are rapidly cooled in a product cooling zone. This ensures a high olefinic yield because the product cooling step slows down the rate of reaction in the gaseous product stream thus preventing further reactions taking place.

Advantageously the gaseous product stream is cooled by injecting a condensate into the gaseous product stream, preferably at multiple points, such that the vaporisation of the condensate cools the gaseous product stream.

The condensate may be a gas or a liquid. When the condensate is gas it is preferably an inert gas. Preferably the condensate is a liquid e.g. water.

Injecting the condensate at high pressure and high temperature ensures that a large proportion of the condensate instantaneously vaporizes at the reactor pressure and therefore provides a very rapid temperature drop in the gaseous product stream. Consequently the condensate, such as water, is usually injected at a pressure higher than the pressure of the gaseous product stream, such as 100 barg and is usually injected at a temperature of between 100-400° C. and preferably between 200-350° C. e.g. 300° C.

Preferably the temperature of the gaseous product stream is reduced to 800° C. preferably to 600° C. within 60 mS preferably 40 mS and advantageously 20 mS from exiting the reaction zone.

BRIEF DESCRIPTION OF THE DRAWINGS

The present invention will now be illustrated with the aid of figures, wherein.

DETAILED DESCRIPTION OF PREFERRED EMBODIMENTS

Figure 1:
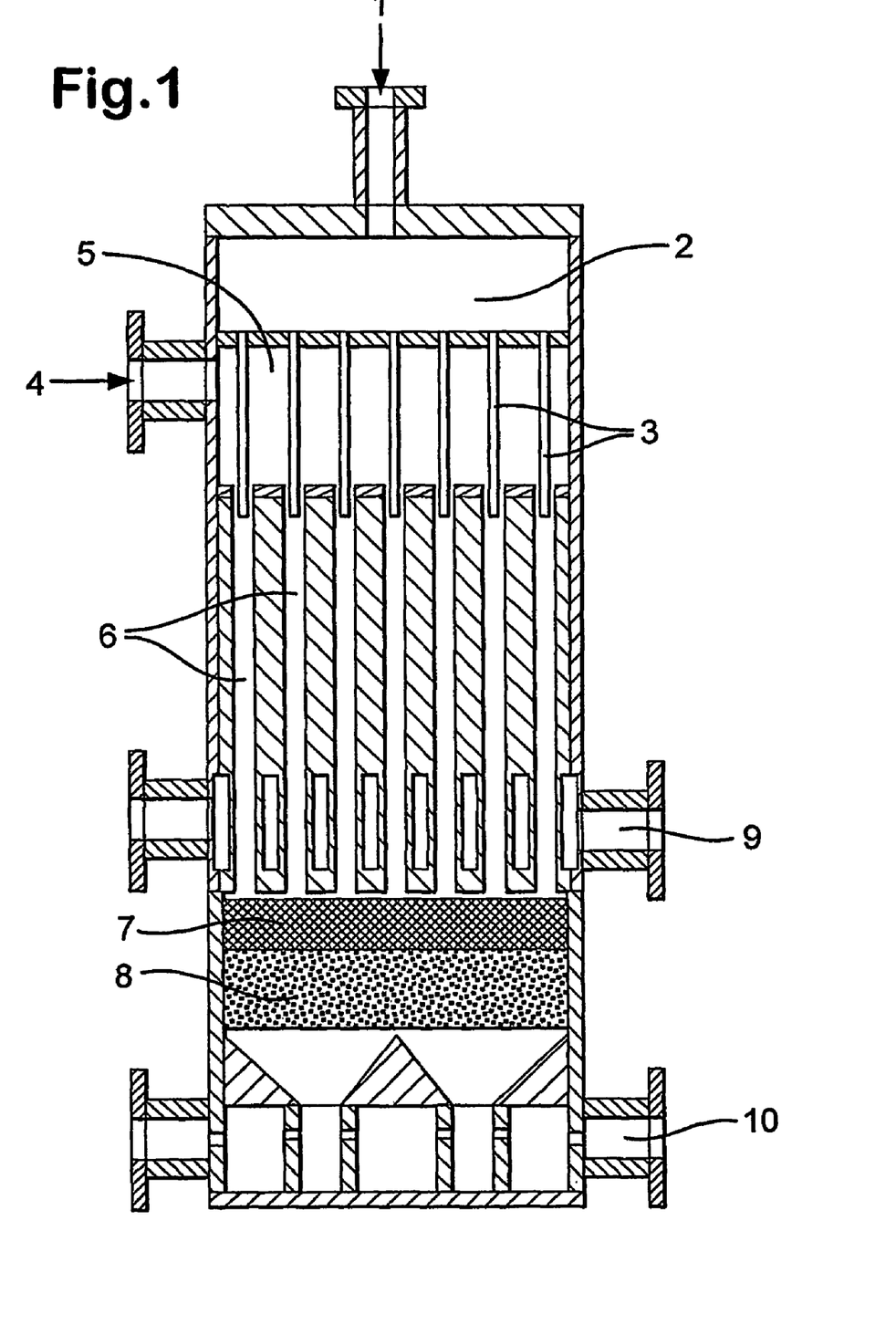
FIG. 1 represents an apparatus according to the first embodiment of the present invention.

In FIG. 1 an oxygen containing gas is passed via a first inlet (1) into a first chamber (2) and then into a plurality of injection tubes (3). A gaseous paraffinic hydrocarbon is passed via second inlet (4) into a second chamber (5) and then into the plurality of conduits (6). The oxygen containing gas is injected via injection tubes (3) into the conduits (6) wherein the gaseous paraffinic hydrocarbon is mixed with the oxygen-containing gas.

The gaseous mixture is then passed to the resistance zone (7) wherein the momentum is taken from the gaseous mixture such that it is passed in a uniform manner to the reaction zone (8) which comprises a catalyst which is capable of supporting combustion beyond the fuel rich limit of flammability. The gaseous reactants are converted in the reaction zone (8) to provide a product stream comprising olefins.

Prior to passing the gaseous mixture to the resistance zone (7) a first cooling zone (9) contacting the downstream end of the plurality of conduits is used to reduce the temperature of the gaseous mixture.

Finally the product stream comprising olefins is passed to a product cooling zone (10) to reduce the temperature of the product stream prior to recovery.

Figure 2A:
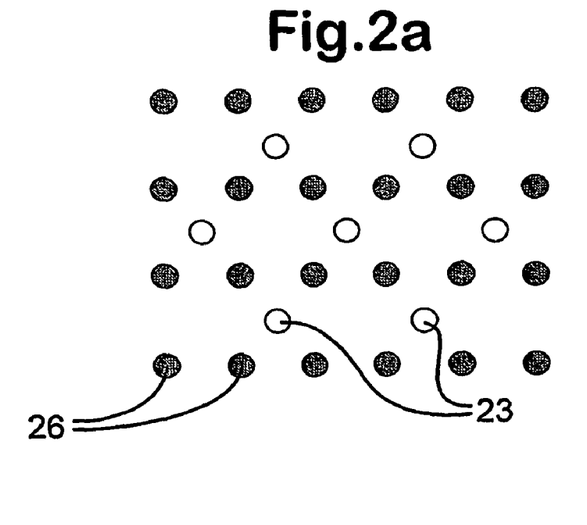
FIG. 2a represents schematically a section of an intermixed configuration of first and second injection tubes for an apparatus according to the second embodiment of the present invention.

In FIG. 2a, a series of first injection tubes (23), shown by open circles, are arranged in a triangular configuration. The exits of the first injection tubes are dispersed amongst the exits of a plurality of second injection tubes (26), which are arranged in a rectangular configuration. In the overall arrangement (the Figure shows just a section) there are approximately twice as many second injection tubes as first injection tubes in this configuration.

Figure 2B:
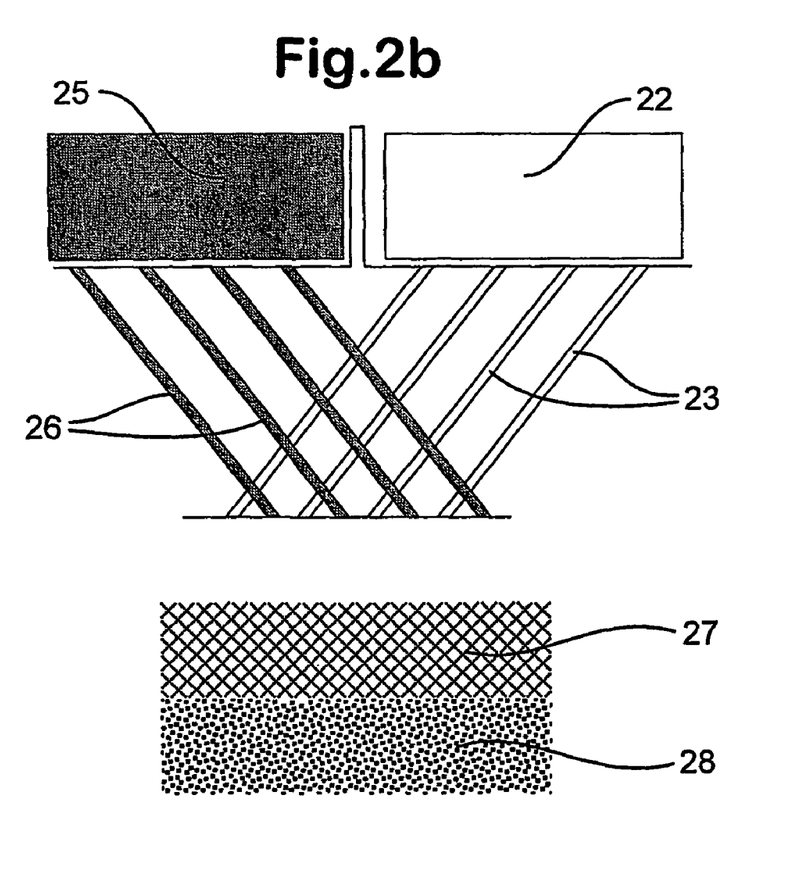
FIG. 2b represents schematically a side view of an apparatus according to the second embodiment of the present invention.

In FIG. 2b an oxygen containing gas is passed into a first chamber (22) and then into the plurality of first injection tubes (23). A gaseous paraffinic hydrocarbon is passed into a second chamber (25) and then into the plurality of second injection tubes (26). The oxygen containing gas and gaseous paraffinic hydrocarbon exit the respective injection tubes and rapidly mix.

The gaseous mixture is then passed to the resistance zone (27) wherein the velocity of the gaseous mixture is smoothed (momentum is taken from the gaseous mixture) such that it is passed in a uniform manner to a reaction zone (28) which comprises a catalyst which is capable of supporting combustion beyond the fuel rich limit of flammability. The gaseous reactants are converted in the reaction zone (28) to provide a product stream comprising olefins.

Finally the product stream comprising olefins is passed to a product cooling zone (not shown) to reduce the temperature of the product stream prior to recovery.

The invention claimed is:

1. A process for the production of a mono-olefin by reacting an oxygen containing gas with a gaseous paraffinic hydrocarbon to form said mono-olefin, said process comprising:
providing an apparatus which comprises:
a first supply means which comprises a plurality of first outlets for delivery of the oxygen containing gas,
a second supply means which comprises a plurality of second outlets for delivery of the gaseous paraffinic hydrocarbon,
a porous resistance zone, and
a reaction zone,
wherein the plurality of first outlets and plurality of second outlets comprises at least 500 first and second outlets per meter squared of the transverse cross-section of the reaction zone, wherein the porous resistance zone is positioned downstream of the first and second supply means with respect to the flow of the oxygen containing gas and the gaseous paraffinic hydrocarbon and is in fluid communication with the first and second supply means, the reaction zone is positioned downstream of the porous resistance zone with respect to the flow of the oxygen containing gas and the gaseous paraffinic hydrocarbon and is in fluid communication with the porous resistance zone, and wherein the first supply means and the second supply means are arranged such that the first gas and the second gas are contacted in an essentially parallel manner and mixed prior to contacting the resistance zone;
passing oxygen containing gas pre-heated to a temperature of 50° to 150° into said first supply means and through said plurality of first outlets;
passing gaseous paraffinic hydrocarbon pre-heated to a temperature of 100° to 400° into said second supply means and through said plurality of second outlets, such that the pre-heated gaseous paraffinic hydrocarbon is contacted in an essentially parallel manner with said pre-heated oxygen containing gas and mixed with the oxygen containing gas to form a gaseous mixture;

passing the said mixture through the porous resistance zone to the reaction zone without passing through a heat exchanger; and partially combusting the gaseous mixture in the reaction zone in the presence of a catalyst which is capable of supporting combustion beyond the fuel rich limit of flammability, to produce the mono-olefin.

2. The process according to claim 1, wherein the apparatus comprises at least 1000 first and second outlets per meter squared of the transverse cross section of the reaction zone.

3. The process according to claim 1, wherein the apparatus comprises a product cooling zone downstream of the reaction zone, wherein the gaseous product stream is rapidly cooled in the product cooling zone by injecting a condensate into the gaseous product stream at multiple points such that the vaporisation of the condensate cools the gaseous product stream.

4. The process according to claim 3, wherein the temperature of the gaseous product stream is reduced to less than 800° C. within 60 ms from exiting the reaction zone.

5. The process according to claim 1, wherein the resistance zone has an average inertial pressure gradient coefficient of between 1000-5000/m.

6. The process according to claim 1, wherein the gaseous paraffinic hydrocarbon is selected from the group consisting of ethane, propane, butane, mixtures of ethane, propane or butane with other hydrocarbons and mixtures of ethane, propane or butane with other materials.

7. A process according to claim 1, wherein the ratio of the gaseous paraffinic hydrocarbon to the oxygen-containing gas mixture is from 5 to 20 times the stoichiometric ratio of hydrocarbon to oxygen-containing gas for complete combustion to carbon dioxide and water.

8. A process according to claim 1, wherein the pressure at the first and second inlets is between 10-50 barg.

9. The process according to claim 1, wherein the first supply means comprises at least one first inlet for supplying the oxygen containing gas to at least one first manifold and a plurality of injection tubes exiting said first manifold for delivery of the oxygen containing gas, and the second supply means comprises at least one second inlet for supplying the gaseous paraffinic hydrocarbon to at least one second manifold and a plurality of conduits exiting said second manifold for delivery of the gaseous paraffinic hydrocarbon, wherein the second manifold is positioned downstream of the first manifold with respect to the flow of the oxygen containing gas, wherein the resistance zone is positioned downstream of the second manifold with respect to the flow of the oxygen containing gas and the gaseous paraffinic hydrocarbon and is in fluid communication with the conduits exiting the second manifold, wherein each conduit comprises an upstream end exiting the second manifold and a downstream end in fluid communication with the resistance zone and wherein the injection tubes exiting the first manifold are arranged such that they extend through the second manifold and project axially into the upstream end of the conduits, wherein the oxygen containing gas is passed into the first manifold and the oxygen-containing gas is injected via the plurality of injection tubes into the plurality of conduits, and wherein the gaseous paraffinic hydrocarbon is passed via the second manifold into the plurality of conduits wherein the gaseous paraffinic hydrocarbon is contacted in an essentially parallel manner and mixed with the oxygen-containing gas.

10. The process according to claim 9, in which the apparatus also comprises a first cooling zone contacting the downstream end of the plurality of conduits exiting the second manifold arranged such that the downstream ends of the plurality of conduits are cooled.

11. The process according to claim 9, wherein the first manifold is a first chamber and the second manifold is a second chamber and the injection tubes exiting the first chamber form a plurality of elongated passageways extending through the second chamber into the upstream end of the plurality of conduits exiting the second manifold.

12. The process according to claim 9, wherein the injection tubes end in a nozzle which provides a restriction at the opening, and which has an internal diameter in the range between 0.5 to 3.0 mm.

13. The process according to claim 9, wherein flow restrictors are provided between the outer surface of the injection tubes and the inner surface of the conduits, at a location at or close to where the injection tubes enter the conduits at the upstream end of the conduits.

14. A process according to claim 1, wherein the first supply means comprises at least one first inlet for supplying the oxygen containing gas to at least one first manifold and a plurality of first injection tubes exiting said first manifold for delivery of the oxygen containing gas, and wherein the second supply means comprises at least one second inlet for supplying the gaseous paraffinic hydrocarbon to at least one second manifold and a plurality of second injection tubes exiting said second manifold for delivery of the gaseous paraffinic hydrocarbon, wherein each injection tube has an exit at the end remote from the manifold and which has a cross-sectional opening of 1 $mm^2$ or less, wherein the exits from the first and second injection tubes are co-located in an intermixed configuration, wherein the oxygen containing gas is passed from the least one first inlet via the least one first manifold to the plurality of the first injection tubes and the gaseous paraffinic hydrocarbon is passed from the least one second inlet via the least one second manifold to the plurality of second injection tubes such that the gaseous paraffinic hydrocarbon is contacted in an essentially parallel manner and mixed with the oxygen-containing gas.

15. The process according to claim 14, wherein there are at least 100000 first and second injection tubes in total per square meter.

16. The process according to claim 15, wherein there are at least 1000000 first and second injection tubes in total per square meter.

17. The process according to claim 14, wherein the exits from the injection tubes are all located in an essentially planar configuration.

18. The process according to claim 14, wherein each injection tube has an exit at the end remote from the manifold which has a cross-sectional opening of 0.5 $mm^2$ or less.

19. The process according to claim 14, wherein the injection tubes are formed as passageways in a diffusion bonded block.

20. Apparatus suitable for reacting a first gaseous reactant with a second gaseous reactant to form a gaseous product, the apparatus being as defined in claim 9.

21. Apparatus suitable for reacting a first gaseous reactant with a second gaseous reactant to form a gaseous product, the apparatus being as defined in claim 14.

22. The process according to claim 5, wherein the resistance zone has an average inertial pressure gradient coefficient of between 2500-3500/m.

23. The process according to claim 6, wherein the other materials are methane, nitrogen, carbon monoxide, carbon dioxide, steam or hydrogen.

24. A process according to claim 8, wherein the pressure at the first and second inlets is between 20-40 barg.

25. The process according to claim 18, wherein each injection tube has an exit at the end remote from the manifold which has a cross-sectional opening of 0.2 mm$^2$ or less.

26. The process according to claim 25, wherein each injection tube has an exit at the end remote from the manifold which has a cross-sectional opening of 0.1 mm$^2$ or less.

27. The process according to claim 1, wherein the oxygen-containing gas is preheated to a temperature of 80 to 120° C. and the gaseous paraffinic hydrocarbon is preheated to 150 to 350° C.

28. The process according to claim 1 wherein the distance of the resistance zone from the ends of the first and second supply means is less than 20 mm.

29. The process according to claim 1 wherein the depth of the resistance zone is 5-100 mm.

30. The process according to claim 1 wherein the porous resistance zone has a permeability which is substantially the same in any direction.

* * * * *